United States Patent
Lemmens et al.

(10) Patent No.: US 7,115,638 B2
(45) Date of Patent: Oct. 3, 2006

(54) AMIDE DERIVATIVE OF AMLODIPINE

(75) Inventors: Jacobus M. Lemmens, Mook (NL); Theodorus H. A. Peters, Arnhem (NL); Franciscus B. G. Benneker, Rheden (NL)

(73) Assignee: Synthon IP Inc., Gainesville, VA (US)

( * ) Notice: Subject to any disclaimer, the term of this patent is extended or adjusted under 35 U.S.C. 154(b) by 45 days.

(21) Appl. No.: 10/435,014

(22) Filed: May 12, 2003

(65) Prior Publication Data

US 2003/0204093 A1 Oct. 30, 2003

Related U.S. Application Data

(60) Division of application No. 09/938,818, filed on Aug. 27, 2001, now Pat. No. 6,602,893, which is a continuation-in-part of application No. 09/809,348, filed on Mar. 16, 2001, now abandoned.

(60) Provisional application No. 60/258,585, filed on Dec. 29, 2000.

(51) Int. Cl.
*A61K 31/455* (2006.01)
*C07D 211/86* (2006.01)

(52) U.S. Cl. .................... 514/356; 546/321

(58) Field of Classification Search ........... 546/321; 514/356

See application file for complete search history.

(56) References Cited

U.S. PATENT DOCUMENTS

| 4,572,909 A | 2/1986 | Campbell et al. |
| 4,879,303 A | 11/1989 | Davison et al. |
| 4,983,740 A | 1/1991 | Peglion et al. |
| 5,155,120 A | 10/1992 | Lazar et al. |
| 5,389,654 A | 2/1995 | Furlan et al. |
| 5,438,145 A | 8/1995 | Furlan et al. |
| 6,046,337 A | 4/2000 | Bozsing et al. |
| 6,479,525 B1 | 11/2002 | Lemmens et al. |
| 6,518,288 B1 | 2/2003 | Lemmens et al. |
| 6,538,012 B1 | 3/2003 | Ettema |
| 6,600,047 B1 | 7/2003 | Benneker et al. |
| 6,602,893 B1 | 8/2003 | Lemmens et al. |

FOREIGN PATENT DOCUMENTS

| EP | 0 089 167 B1 | 10/1986 |
| EP | 0 244 944 | 1/1990 |
| EP | 0 290 211 B1 | 9/1991 |
| EP | 0 534 520 B1 | 3/1997 |
| EP | 0 902 016 A1 | 3/1999 |
| EP | 0 963 980 A2 | 12/1999 |
| EP | 1266654 A1 | 12/2002 |
| WO | 99/25688 | 5/1999 |
| WO | 99/52873 | 10/1999 |
| WO | 00/24714 | 5/2000 |
| WO | 00/35873 | 6/2000 |
| WO | 00/35910 | 6/2000 |

OTHER PUBLICATIONS

Alker et al., "Long-acting dihydropyridine calcium antagonists. 9. Structure activity relationships around amlodipine", Eur J Med Chem (1991) 26, 907-913.
Amlodipine Besylate Monograph, PHARMEUROPA vol. 10, No. 2, 197-198, Jun. 1998.
Faulkner et al, "Absorption of Amlodipine Unaffected by Food", Arzneim Forsch/Drug Res. 39 (11), No. 7, (1989).
McDaid and Deasy, "Formulation development of a transdermal drug delivery system for amlodipine base", International Journal of Pharmaceutics 133 (1996) 71-83.
Arrowsmith et al., "Long-Acting Dihydropyridine Calcium Antagonists. 1. 2-Alkoxymethyl Derivatives Incorporating Basic Substituents", J. Med. Chem. American Chemical Society, 1986, 29, 1696-1702.
FDA FOIA Material on Amlodipine Besylate, NDA No. 19-787, "Review of an Original NDA", Oct. 10, 1990.

*Primary Examiner*—Patricia L. Morris
(74) *Attorney, Agent, or Firm*—Mark R. Buscher

(57) ABSTRACT

A derivative of amlodipine having the following formula is useful as a pharmaceutical, either alone or in combination with amlodipine, in treating angina and hypertension 9 Claims, 1 Drawing Sheet

AMIDE DERIVATIVE OF AMLODIPINE

This application is a divisional application under 35 U.S.C. § 121 of prior application Ser. No. 09/938,818, filed Aug. 27, 2001, now U.S. Pat. No. 6,602,893, which is a continuation in part under 35 U.S.C. § 120 of prior U.S. patent application Ser. No. 09/809,348, filed Mar. 16, 2001, now abandoned, both of which claim the benefit of priority under 35 U.S.C. § 119(e) from provisional application Ser. No. 60/258,585, filed Dec. 29, 2000. The entire contents of application Ser. Nos. 09/938,818, 09/809,348, and 60/258,585 are incorporated herein by reference.

BACKGROUND OF THE INVENTION

1. Field of the Invention

The present invention relates to a novel compound, to processes for preparing it and to its use in treating medical disorders. In particular the present invention relates to a novel derivative of Amlodipine.

2. Description of the Related Arts

Calcium channel blockers (calcium antagonists) are useful in treating cardiac conditions including angina and/or hypertension. Dicarboxylate-dihydropyridine derivatives are generally known to possess calcium channel blocking activity. For example, EP 089 167 and corresponding U.S. Pat. No. 4,572,909 disclose a class of 2-amino group, 3,5-dicarboxylate dihydropyridine derivatives as being useful calcium channel blockers. These patents identify that one of the most preferred compounds is 2-[(2-aminoethoxy)methyl]-4-(2-chlorophenyl)-3-ethoxycarbonyl-5-methoxycarbonyl-6-methyl-1,4-dihydropyridine. This compound, which is now commonly known as amlodipine, has the following formula:

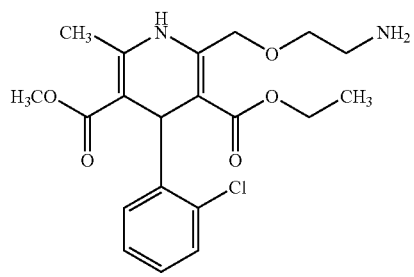

Amlodipine exhibits good bioavailability and has a long half-life in the body. While a variety of acid addition salts are taught in these patents to be suitable, the maleate salt is identified as the most preferred acid addition salt. However, the commercial product of amlodipine (NORVASC by Pfizer) uses amlodipine besylate (benzene sulfonate) and not amlodipine maleate. Indeed, subsequent patents EP 244 944 and corresponding U.S. Pat. No. 4,879,303 indicate that the besylate salt provides certain advantages over the known salts including good formulating properties. Apparently, amlodipine maleate suffered from tabletting and stability problems so as to cause a switch during development to the besylate salt. (See "Review of Original NDA" for NDA# 19-787 of 10.10.1990, obtainable from FDA under Freedom of Information Act). The stability and tabletting issues/causes are not publicly disclosed in the information available from the FDA.

SUMMARY OF THE INVENTION

The present invention relates to the discovery of a novel derivative of amlodipine, the use thereof, and methods of making the same. Specifically, the present invention provides a compound of the following formula (1):

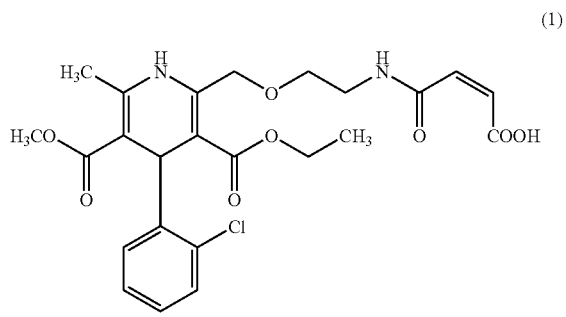

or a pharmaceutically acceptable salt thereof.

The compound of formula (1) is useful as a calcium channel blocker and thus further aspects of the invention relate to a pharmaceutical composition comprising an effective amount of a compound of formula (1) or a pharmaceutically acceptable salt thereof and a pharmaceutically acceptable excipient as well as a method of treating angina or hypertension by administering to a patient in need thereof an effective amount of a compound of formula (1) or a pharmaceutically acceptable salt thereof. Further, the present invention can be used in combination with amlodipine as a pharmaceutically active ingredient composition. The compound of formula (1) can be made by a process that comprises reacting amlodipine or a salt thereof with a carbonyl-activated maleic acid compound.

DETAILED DESCRIPTION OF THE INVENTION

Figure 1:
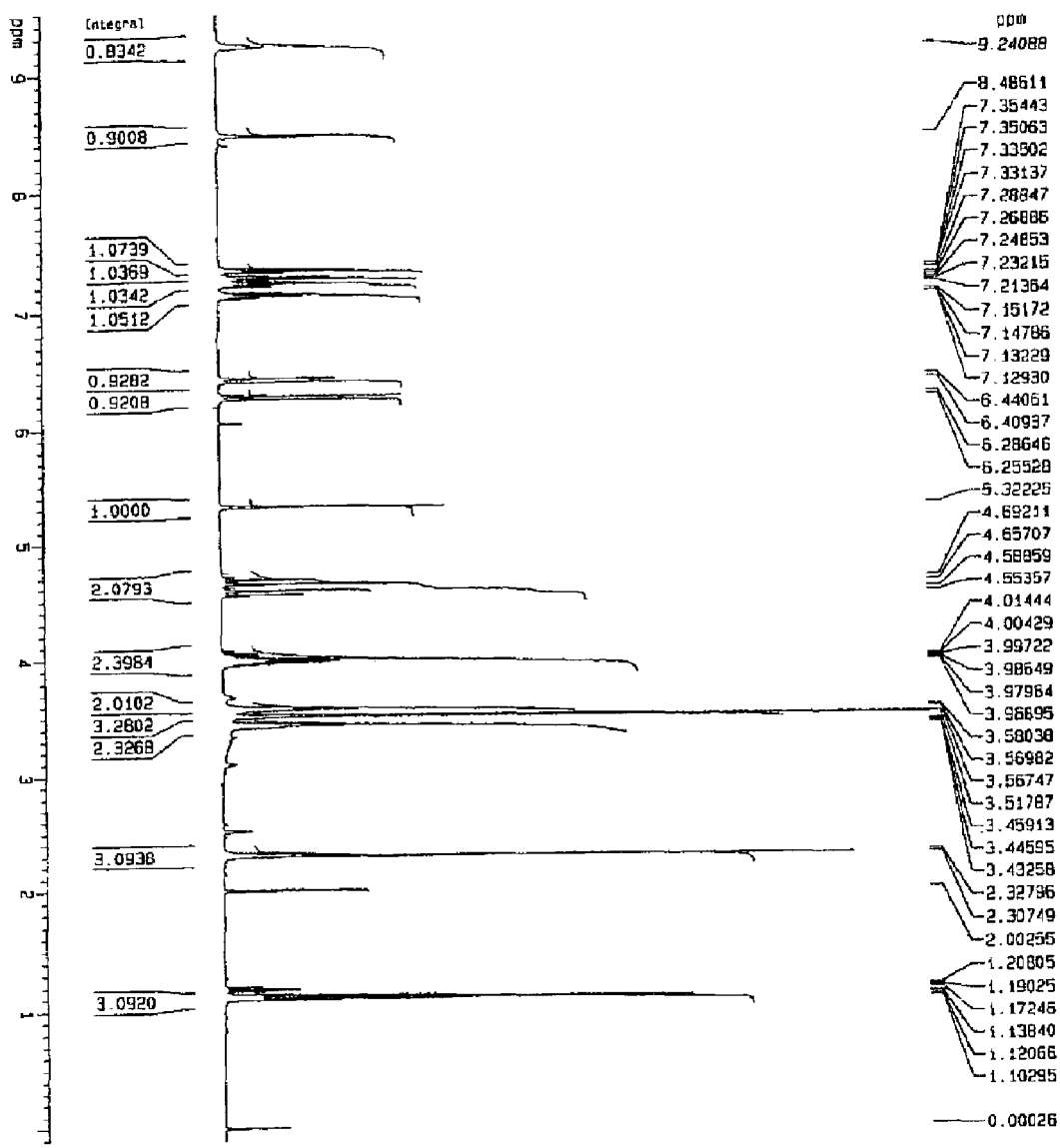
FIG. 1 shows the $^1$H-NMR spectrum for the material of Example 1.

The compound of formula (1) can be described as (Z)-4-[(2-{[4-(2-chlorophenyl)-3-(ethoxycarbonyl)-5-(methoxycarbonyl)-6-methyl-1,4-dihydro-2-pyridinyl]methoxy}ethyl)amino]-4-oxo-2-butenoic acid. It is understood that the compound represented by formula (1) may exist as the free acid form or as the corresponding zwitter ion form and that while both forms are included within the meaning of the structural formula, for simplicity sake, only the free acid form is shown. Further, while the compound of formula (1) is referred to in the singular, it should be understood that the compound can exist as one of two isomers caused by a chiral center on the 1,4-dihydropyridine ring or as a mixture of isomers: all are embraced by the singular "compound."

The compound of formula (1) can be in the form of a salt and is typically a pharmaceutically acceptable salt. Salts include those formed with a metal cation such as an alkali metal cation; those formed with ammonia or an amine compound including mono-, di-, or tri-alkylamine compounds and ring amine compounds; or with an acid. More specifically, metal salts include sodium, potassium and lithium salts of the compound of formula (1). Ammonia and amine salts include salts made with ammonium, methylamine, dimethylamine, triethylamine, pyridine, and amlodipine. Suitable acid salts include inorganic and organic acids such as hydrochloric, sulfuric, phosphoric, acetic, propionic, maleic, fumaric, tartaric, benzoic, methane sulfonic, and benzene sulfonic acid. Salts can also be formed with ambivalent compounds such as aminoacids, e.g. glycine or alanine. Preferred salts include salts made with a pharmaceutically acceptable acid, especially maleic acid. Another preferred salt is the salt formed with amlodipine and the compound of formula (1), especially in a 1:1 molar ratio of the compound of formula (1) with amlodipine.

The compound of formula (1) and its salts are normally solid at room temperature and can be crystalline or amorphous. The crystalline forms include anhydrate forms, hydrated forms and solvate forms. The compound may be isolated and thus of relatively high purity, typically greater than 50 wt % pure, preferably greater than 75 weight % pure, more preferably greater than 95 weight % pure. However, relatively impure forms are also included as are dissolved forms.

The compound of formula (1) can be made by reacting amlodipine or a salt thereof with a carbonyl-activated maleic acid compound. The reaction is essentially an amidation reaction and thus is favored by the presence of an acid catalyst, elevated temperature, etc., and such other amidation conditions as are well known by workers skilled in the art. A "carbonyl-activated maleic acid compound" means maleic acid or a derivative thereof that has a sufficiently activated carbonyl group to facilitate the amidation reaction with amlodipine. In some embodiments the carbonyl activation is achieved by the presence of an acid catalyst, typically a Lewis acid such as aluminium chloride or phosphoric acid. However, the preferred embodiment is to use maleic acid anhydride which provides an activated carbonyl group without the necessity of a catalyst. Maleic acid per se and in the absence of a catalyst or activator is not a carbonyl-activated maleic acid compound and will not readily form a compound of formula (1) even if placed in the presence of amlodipine. The reaction with maleic acid anhydride is set forth below.

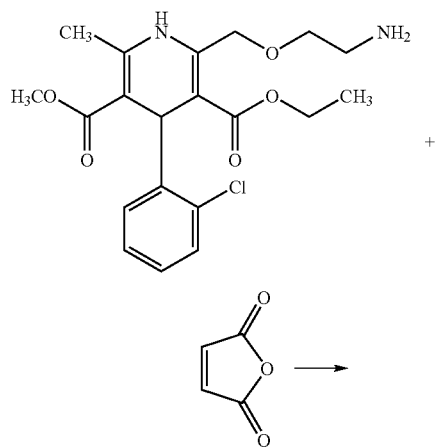

-continued

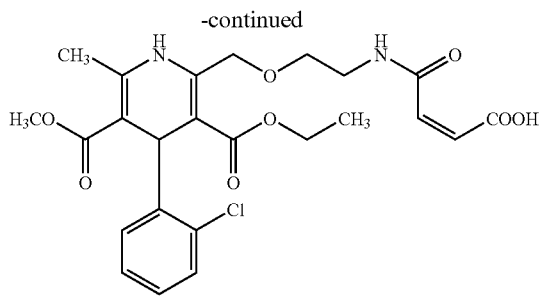

In general, the formation reaction of the compound of formula (1) can be carried out by bringing amlodipine free base or a salt thereof and the activated-carbonyl maleic acid compound into intimate contact with each other. Preferably, the reaction is carried out at an elevated temperature such as 25–100° C., more typically 35–50° C., and in an appropriate solvent. Among solvents suitable for the addition reaction are polar aprotic solvents, for example N,N-dimethylformamide, alcohols such as ethanol and isopropanol, esters such as ethyl acetate, and hydrocarbons such as toluene. The amlodipine and carbonyl-activated maleic acid compound are normally combined in approximately stoichiometric ratios, namely 0.9:1 to 1:0.9. However, excess amlodipine may advantageously be used in the case where the amlodipine salt of the compound of formula (1) is desired. Also, in cases where a mixture of amlodipine and a compound of formula (1) is desired, as discussed more fully hereinafter, a large molar excess of amlodipine to activated-carbonyl maleic acid compound may be used, e.g. up to 50:1, more typically up to 20:1, and generally 2:1 to 10:1 of amlodipine to carbonyl-activated maleic acid compound on a molar basis. Also, in this embodiment, a non-activated-carbonyl maleic acid may be simultaneously provided along with the activated carbonyl maleic acid compound to form a mixture of amlodipine maleate salt and a compound of formula (1).

Amlodipine free base may be prepared according to the procedures generally outlined in U.S. Pat. No. 4,572,909. Another useful synthesis scheme for making amlodipine or salts thereof in good yields and purity via a phthalimidoamlodipine intermediate is described in commonly-owned provisional application Ser. No. 60/258,613, filed Dec. 29, 2000, the entire contents of which are incorporated herein by reference, and in commonly-owned co-pending U.S. patent application Ser. No. 09/809,351, filed on Mar. 16, 2001, and entitled "Process for Making Amlodipine, Derivatives Thereof, and Precursors Therefor," the entire contents of which are incorporated herein by reference. Maleic acid and its anhydride as well as acid catalysts are all commercially available.

The compound (1) may be isolated from the reaction medium by conventional methods such as evaporation or precipitation, and may be purified by crystallization, for example at reflux temperature in an appropriate solvent, for example an ester such as ethyl acetate, an alcohol such as propan-2-ol, or a ketone such as acetone. The stereoisomers may be separated by crystallization or chromatography, optionally in the form of a salt, for example as salt with an optically active base or acid by methods generally known in the art.

Treatment of compound (1) with an equivalent amount of an acid such as maleic acid optionally followed by an isolation step such as precipitation, evaporation or lyophilization, produces an acid addition salt of the compound of formula (1) with the acid. Other salts of compound (1) may be formed by reaction with an equivalent amount of a base, such as for example sodium hydroxide to form a sodium salt of the compound of formula (1).

The compound of formula (1) and its pharmaceutically acceptable salts are useful calcium channel blockers and thus can be used to treat any cardiac condition that would be benefited by administration of a calcium channel blocker. Additionally, the compound of formula (1) is convertable to amlodipine by hydrolysis of the amide bond. Hydrolysis of the amide bond can occur in vivo, e.g. by metabolization in the body after administration. Accordingly, the compound of formula (1) and its pharmaceutically acceptable salts can be used as a "pro-drug" for amlodipine and thus can be used in the same fashion and are useful in treating the same cardiac conditions as amlodipine.

In particular, the compound of formula (1) and its pharmaceutically acceptable salts can be used to treat or prevent hypertension or angina by administering an effective amount to a patient in need thereof. The specific form of angina is not particularly limited and specifically includes chronic stable angina pectoris and vasospastic angina (Prinzmetal's angina). The compound can be administered by any suitable route including orally or parenterally. The "patients" intended to be treated include human and non-human animals especially non-human mammals.

The compound is usually administered as part of a pharmaceutical composition. Accordingly, a further aspect of the invention is a pharmaceutical composition for treating or preventing hypertension or angina that comprises an effective amount of a compound of formula (1) or a pharmaceutically acceptable salt thereof and a pharmaceutically acceptable excipient. Excipients include any inert or non-active material used in making a pharmaceutical dosage form. For example, tablet excipients include, but are not limited to, calcium phosphate, cellulose, starch or lactose. Capsules such as those made of gelatin, may contain or carry the compound of formula (1) or a pharmaceutically acceptable salt thereof alone or in admixture with other excipients. Liquid dosage forms are also included such as oral liquids in the form of liquors or suspensions, as well as injectable solutions. The pharmaceutical composition may be formulated for transdermal administration in the form of a patch. All of the above-described pharmaceutical compositions may optionally contain one or more of each of the following excipients: carriers, diluents, colorants, flavoring agents, lubricants, solubilizing agents, disintegrants, binders and preservatives.

The pharmaceutical composition is normally provided in a unit dose. A unit dose is typically administered once or twice daily, more typically once daily. In the case of a transdermal patch, the unit dose (one patch) is generally applied at least once a month, more commonly at least once a bi-week, and typically once a week. An effective amount of the compound of formula (1) or a pharmaceutically acceptable salt thereof in a unit dose for treating or preventing hypertension or angina is generally within the range of 1 to 100 mg, typically 1 to 50 mg, more typically 1 to 20 mg. In solid oral dosage forms (tablets, capsules, etc.), the pharmaceutical composition typically contains about 1, 2.5, 5.0, or 10 mg of the compound of formula (1) or a pharmaceutically acceptable salt thereof. For simplicity, all amounts refer to the corresponding amount of free base provided to the composition.

Another embodiment of the invention relates to the use of a mixture of the compound of formula (1) or a pharmaceutically acceptable salt thereof with amlodipine or a pharmaceutically acceptable salt thereof. The combination of these two pharmaceutically active agents can form a useful pharmaceutically active ingredient composition. Generally, the pharmaceutically active ingredient composition comprises (a) 100 parts by weight of amlodipine or a pharmaceutically acceptable salt thereof and (b) about 0.1 to about 1000 parts by weight, usually 0.5 to 500 parts by weight, more typically 2 to 100 parts by weight of a compound of formula (1) or a pharmaceutically acceptable salt thereof. The amlodipine is preferably in the form of an acid addition salt, especially the maleate salt. The compound of formula (1) is preferably an acid addition salt, especially the maleate salt, or an amlodipine salt or a mixture thereof. The blend may be obtained directly by controlling the ratio of carbonyl-activated maleic acid compound to non-carbonyl-activated maleic acid and/or to the amount of amlodipine. Alternatively, the pharmaceutically active ingredient composition can be formed by blending the amlodipine compound with the compound of formula (1) (or their respective salt forms, etc.) in the desired ratio.

The pharmaceutically active ingredient composition can be used in like manner as the compound of formula (1) to form a pharmaceutical composition for treating hypertension or angina. Specifically, such a pharmaceutical composition comprises an effective amount of the pharmaceutically active ingredient composition and a pharmaceutically acceptable excipient as previously described. Similarly the unit dose contains between 1 and 100 mg, typically 1 to 50 mg, more typically 1 to 20 mg and specifically the solid oral dosage forms (tablets, capsules, etc.) typically contain about 1, 2.5, 5.0, or 10 mg of the pharmaceutically active ingredient composition. For simplicity the stated amounts refer to the weight corresponding to the sum of the free base of the amlodipine and the compound of formula (1).

The pharmaceutically active ingredient composition per se or in the form of a pharmaceutical composition can be used to treat or prevent hypertension or angina by administering an effective amount to a patient in need thereof.

All of the pharmaceutical compositions described above can be made by known methods and techniques. For example, the tablets can be made by dry granulation/direct compression or by a classical wet granulation method. Similarly, capsules can be made by blending the ingredients and filling the capsule. A suitable pharmaceutical composition for the above-described pharmaceutically active ingredient composition, having good stability can be obtained by selecting the excipients so as to have a pH of less than 7.0, when measured as a 20 wt % aqueous slurry, as is more fully described in commonly-owned co-pending U.S. patent application Ser. No. 09/809,346, filed, on Mar. 16, 2001, and entitled "Pharmaceutical Compositions Comprising Amlodipine Maleate," the entire contents of which are incorporated herein by reference.

Another use of the amlodipine maleamide of formula (1) is as a reference standard or reference marker for evaluating the purity of amlodipine maleate and pharmaceutical compositions comprising amlodipine maleate as is more fully described in commonly-owned U.S. patent application Ser. No. 09/809,347, filed on Mar. 16, 2001, and entitled "Reference Standard For Determining The Purity or Stability of Amlodipine Maleate and Processes Therefor" the entire contents of which are incorporated herein by reference.

The following Examples illustrate the invention.

EXAMPLE 1

Preparation of the Compound of Formula (1)

5 g of amlodipine was dissolved in 50 ml of ethyl acetate and heated to 60° C. To this mixture was added 1.15 g of maleic anhydride and the mixture was shaken until the solution was clear. The mixture was cooled to room temperature and left overnight. The mixture was evaporated to dryness and subsequently dried in a high vacuum oven at 25° C. for 3 hours leaving a yellow solid.

Yield: 6.1 g (99%)
Mp: 83° C.–86° C.
Purity: greater than 95% (HPLC)
$^1$H-NMR Spectrum:

The $^1$H-NMR spectrum was measured at 303 K on a Bruker Avance-400 in deuterated dimethylsulfoxide at 400 MHz. The spectrum is shown on FIG. 1. δ Assignment 1.12 (t, 3H, $J_{11,12}$=7.0 Hz, 12-H3)
2.31 (s, 3H, 15-H$_3$)
3.44 (bq, ~2H, 9-H$_2$)
3.52 (s, ~3H, 14-H$_3$)
3.58 (bt, 2H, 8-H$_2$)
3.99 (m, ~2H, 11-H$_2$)
4.62 (AB q, 2H, 7-H$_2$)
5.32 (s, 1H, 4-H)
6.27 (d, ~1H, $J_{4'',5'}$=12.4 Hz, 4''-H)
6.43 (d, ~1H, $J_{4'',5''}$=12.4 Hz, 5''-H)
7.13 (dt, 1H, $J_{3',4'}$=$J_{4',5'}$=7.7 Hz, $J_{4',6'}$=1.6 Hz, 4'-H)
7.23 (dt, 1H, $J_{4',5'}$=$J_{5',6'}$=7.7 Hz, $J_{3',5'}$=1.0 Hz, 5'-H)
7.28 (dd, 1H, $J_{3',4'}$=7.7 Hz, $J_{3',5'}$=1.0 Hz, 3'-H)
7.34 (dd, 1H, $J_{4',6'}$=1.6 Hz, $J_{5',6'}$=7.7 Hz, 6'-H)
8.49 (s, ~1H, 1-H)
9.24 (bt, ~1H, 9'-NH)

EXAMPLE 2

Preparation of a Mixture of Amlodipine Maleate and Amlodipine Amide 5 g of amlodipine was dissolved in 50 ml of ethyl acetate at 60° C. To the solution, 1.28 g of maleic acid and 0.12 g of maleic acid anhydride were added and the mixture was shaken until clear. The mixture was slowly cooled to room temperature during which time a solid precipitated. The solid was filtered off and washed with 10 ml of ethyl acetate. After drying in a vacuum oven at 35° C. for 18 hours, 5.55 g of a solid was obtained.

According to HPLC analysis, the content of the compound of formula (1) related to amlodipine maleate was 1.8%.

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

What is claimed is:

1. An amine salt of a compound of formula (1)

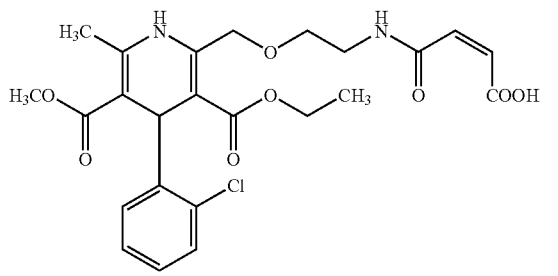

(1)

wherein said amine salt is an amlodipine salt of said compound.

2. A pharmaceutically active ingredient composition comprising amlodipine or a pharmaceutically acceptable salt thereof and a compound of formula (1)

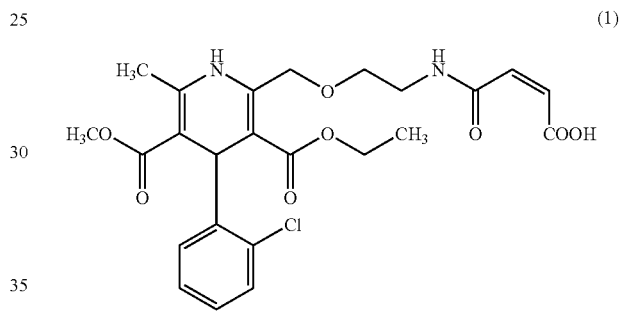

(1)

or a pharmaceutically acceptable salt thereof.

3. The composition according to claim 2, wherein said composition comprises 100 parts by weight of said amlodipine and 0.1 to 1000 parts by weight of said compound of formula (1).

4. The composition according to claim 3, wherein said composition comprises said compound of formula (1) in an amount of 0.5 to 500 parts by weight.

5. The composition according to claim 3, wherein said composition comprises 100 parts of amlodipine maleate and 2 to 100 parts of the maleate salt, the amlodipine salt, or both salt forms, of said compound of formula (1).

6. A pharmaceutical composition for treating angina or hypertension comprising an effective amount of the pharmaceutically active ingredient composition according to claim 2 and a pharmaceutically acceptable excipient.

7. The pharmaceutical composition according to claim 6, wherein said pharmaceutical composition is a unit dose form.

8. The pharmaceutical composition according to claim 7, wherein said effective amount of said pharmaceutically active ingredient composition is within the range of 1 to 20 mg.

9. A process for treating angina or hypertension which comprises administering to a patient in need thereof an effective amount of a pharmaceutically active ingredient composition according to claim 2.

* * * * *